(12) United States Patent
Chen

(10) Patent No.: US 10,596,790 B1
(45) Date of Patent: Mar. 24, 2020

(54) MULTILAYERED ELASTOMERIC ARTICLES AND METHODS THEREOF

(71) Applicant: Fung Bor Chen, Greer, SC (US)

(72) Inventor: Fung Bor Chen, Greer, SC (US)

( * ) Notice: Subject to any disclaimer, the term of this patent is extended or adjusted under 35 U.S.C. 154(b) by 0 days.

(21) Appl. No.: 15/870,962

(22) Filed: Jan. 14, 2018

(51) Int. Cl.
| | | |
|---|---|---|
| *B32B 27/32* | (2006.01) | |
| *B32B 27/30* | (2006.01) | |
| *B32B 3/30* | (2006.01) | |
| *A61B 42/10* | (2016.01) | |

(52) U.S. Cl.
CPC ............... *B32B 27/32* (2013.01); *B32B 3/30* (2013.01); *B32B 27/302* (2013.01); *B32B 27/306* (2013.01); *B32B 27/308* (2013.01); *A61B 42/10* (2016.02); *B32B 2250/246* (2013.01); *B32B 2255/26* (2013.01); *B32B 2305/72* (2013.01); *B32B 2307/51* (2013.01); *B32B 2437/02* (2013.01)

(58) Field of Classification Search
None
See application file for complete search history.

(56) References Cited

U.S. PATENT DOCUMENTS

| | | | | |
|---|---|---|---|---|
| 363 A | * | 6/1844 | Goodyear ............... | B29C 41/14 264/233 |
| 4,575,476 A | * | 3/1986 | Podell ................... | A61B 42/10 128/846 |
| 5,447,783 A | * | 9/1995 | Horn ...................... | A41D 31/02 428/216 |
| 5,612,083 A | * | 3/1997 | Haung .................... | B29C 41/14 264/233 |
| 5,649,326 A | * | 7/1997 | Richard, Jr. .......... | A61F 13/041 2/161.7 |
| 6,495,612 B1 | * | 12/2002 | Corzani ................ | A61L 15/225 523/105 |
| 6,706,313 B1 | | 3/2004 | Goldstein et al. | |
| 8,110,266 B2 | | 2/2012 | Chen et al. | |
| 9,579,426 B2 | | 2/2017 | Chen et al. | |
| 2004/0091557 A1 | * | 5/2004 | Hamann ............... | A61K 8/0208 424/727 |
| 2005/0132466 A1 | * | 6/2005 | Janssen ................... | A61L 31/10 2/159 |
| 2006/0141186 A1 | * | 6/2006 | Janssen ...................... | C08J 5/02 428/35.7 |

(Continued)

*Primary Examiner* — Callie E Shosho
*Assistant Examiner* — John Vincent Lawler
(74) *Attorney, Agent, or Firm* — Fox Rothschild LLP

(57) ABSTRACT

Disclosed is a multilayered elastomeric article with hydrophobic polymers as a patient contacting surface, hydrophilic polymers as a wear contacting surface, and a blend of the hydrophobic and the hydrophilic polymers as an intermediate layer between two contacting surfaces. The article has low water absorption of the patient contacting surface to prevent virus penetration and a textured surface of the wear contacting surface to reduce the friction force between hand and glove surface. The hydrophilic polymers in wear contacting and intermediate layers of the article can increase water absorption and boost leaching effectiveness. High water absorption minimizes the uncomfortable feelings from excessive sweating. Increased effectiveness in leaching makes the article less cytotoxic. A method for making the disclosed elastomeric article is also provided.

4 Claims, 5 Drawing Sheets

A finished glove 2 with line A-A for sectional view in FIG. 2B

(56) References Cited

U.S. PATENT DOCUMENTS

| | | | |
|---|---|---|---|
| 2007/0104766 A1* | 5/2007 | Wang | A61B 42/10 424/443 |
| 2009/0191248 A1* | 7/2009 | Hoffman | A61K 8/43 424/402 |
| 2010/0233223 A1* | 9/2010 | Eng | A61L 31/10 424/404 |
| 2017/0107403 A1 | 4/2017 | Woo et al. | |

* cited by examiner

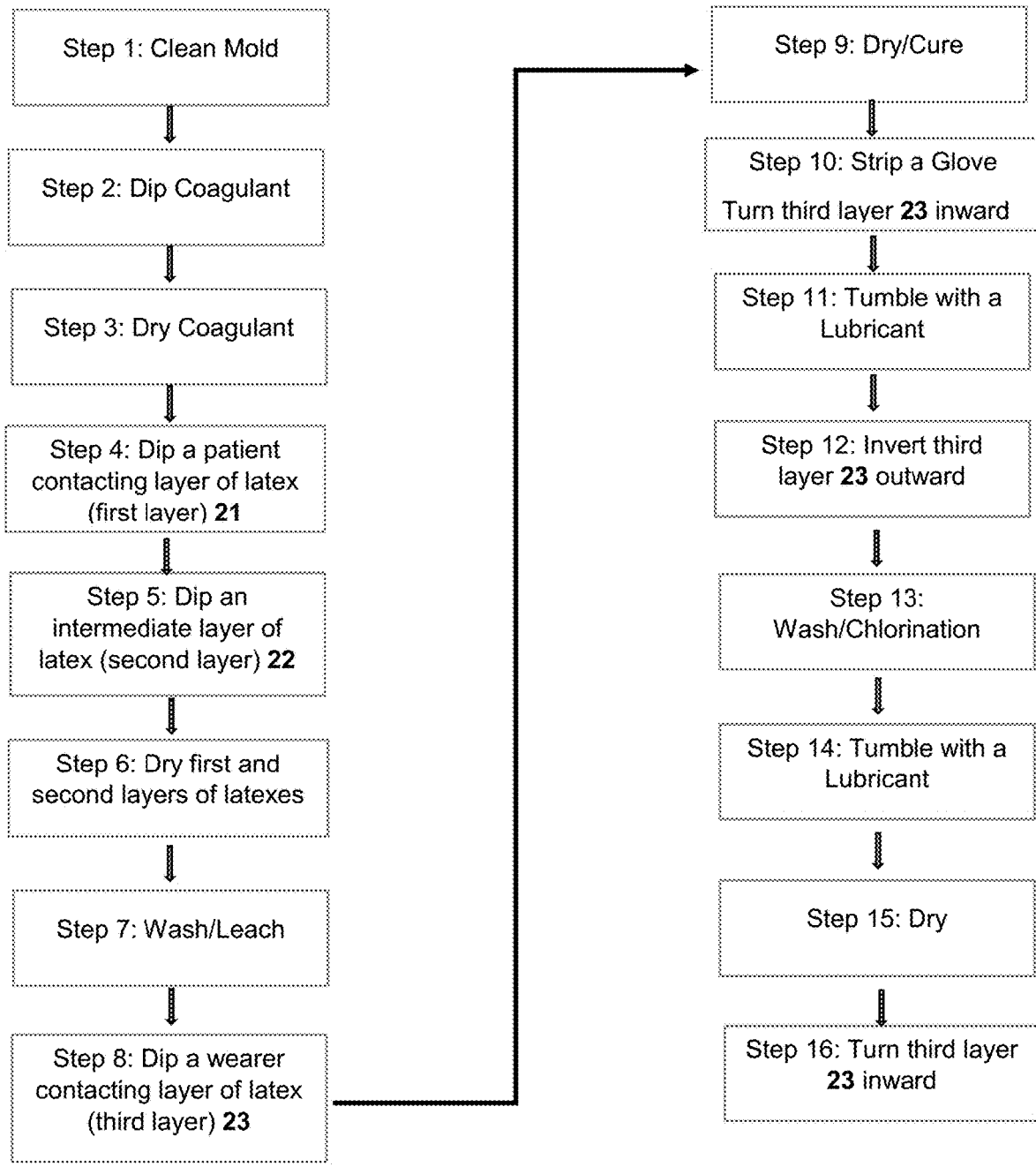
FIG. 1 A glove process flow chart

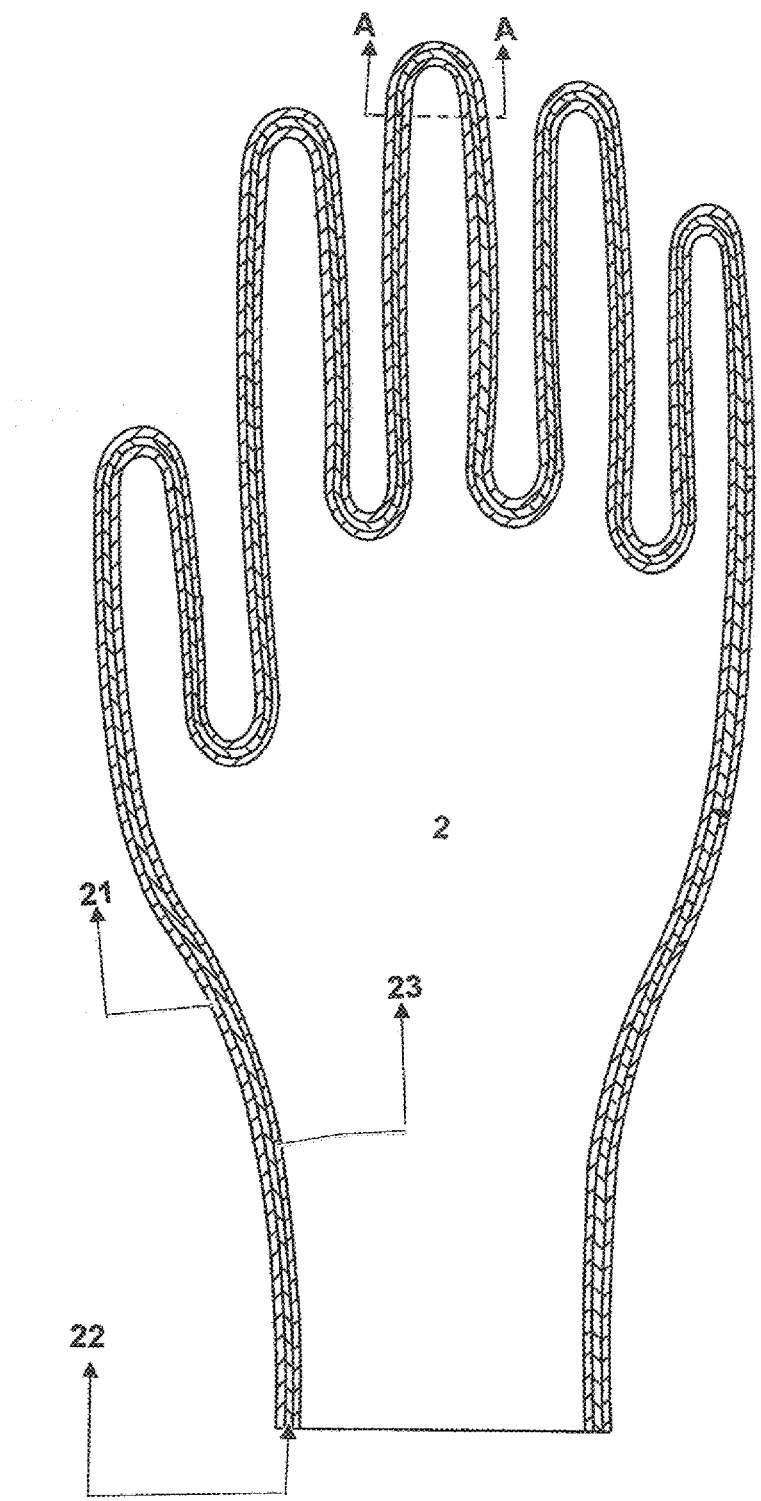
FIG. 2A  A finished glove 2 with line A-A for sectional view in FIG. 2B

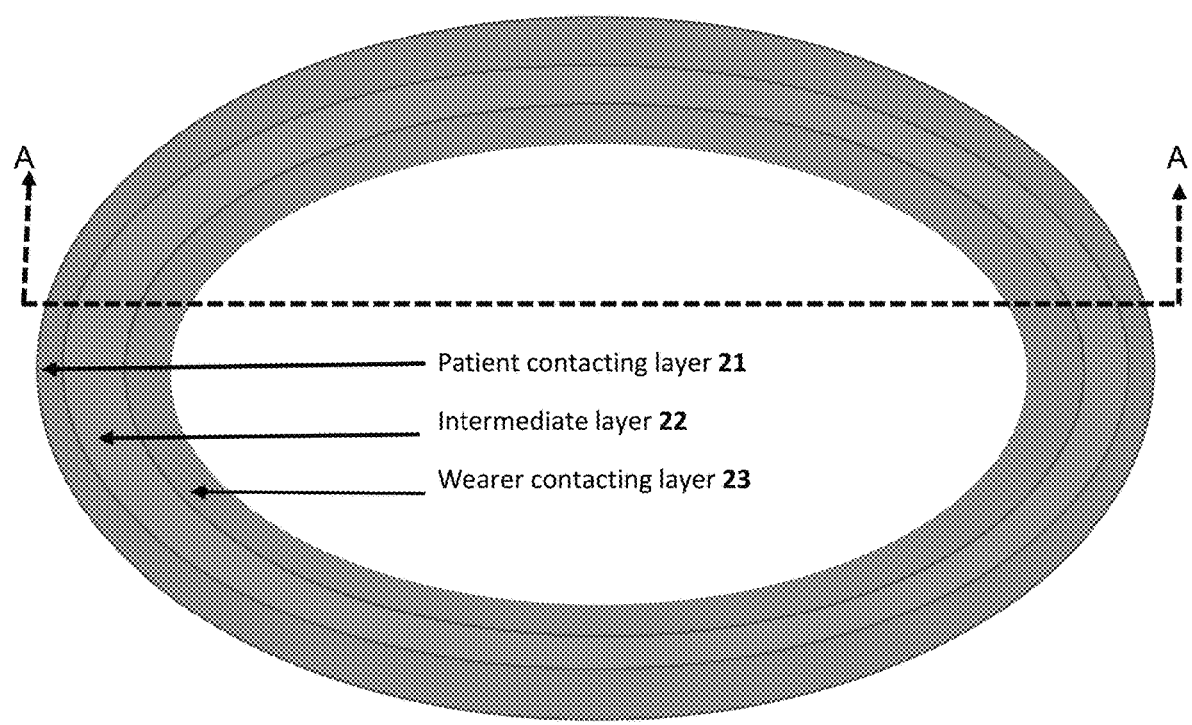
FIG. 2B  A sectional view of a finished glove 2 along line A-A of FIG. 2A

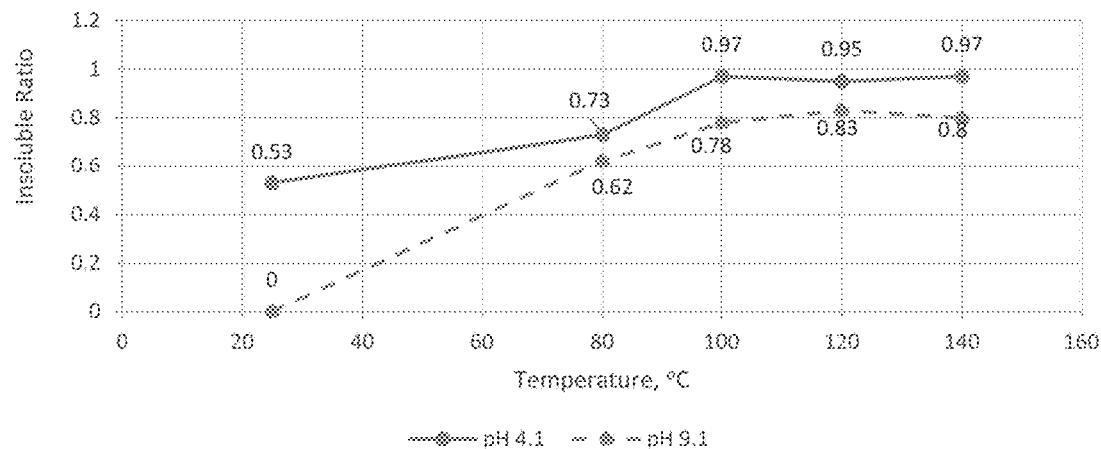
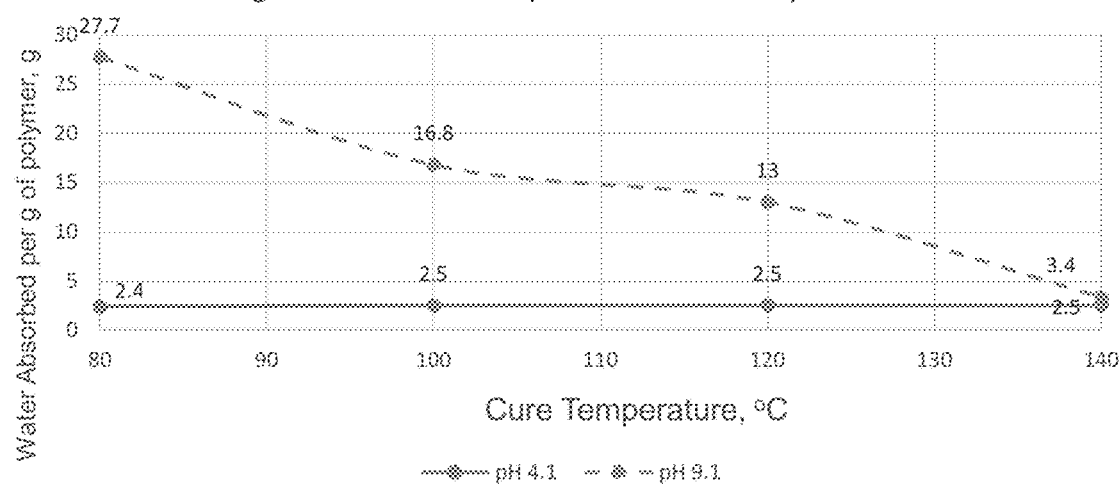

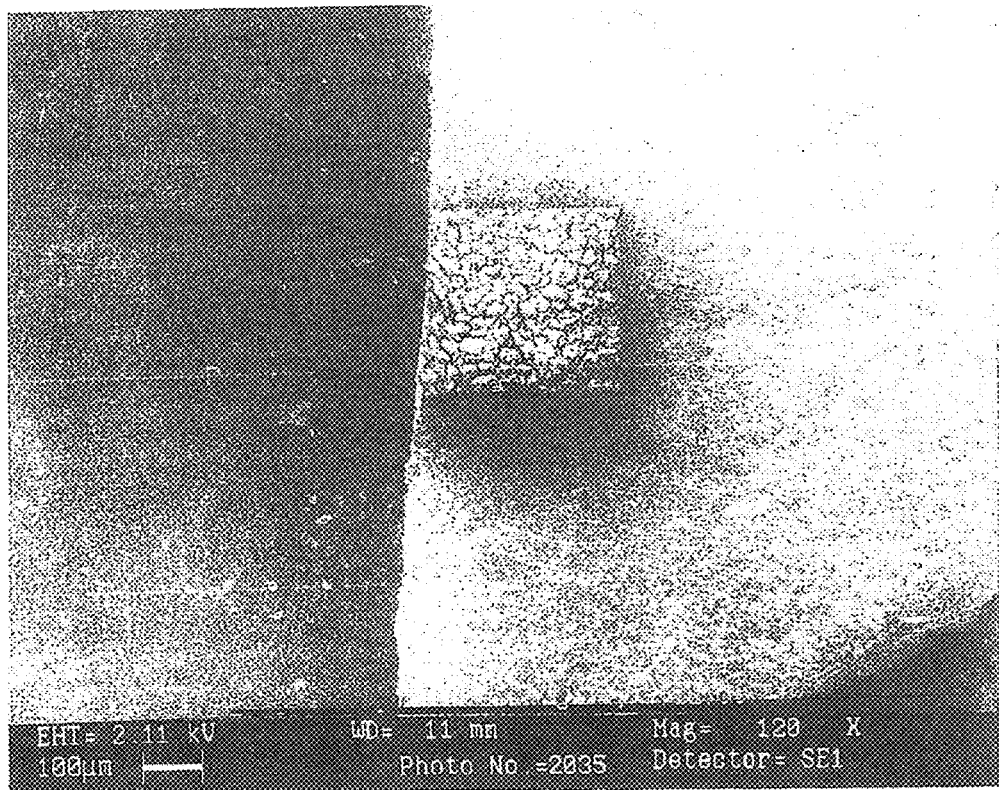
FIG. 5 A close-up SEM image taken at the third layer surface of a finished glove 2

MULTILAYERED ELASTOMERIC ARTICLES AND METHODS THEREOF

FIELD OF INVENTION

The present invention generally relates to multilayered elastomeric articles, and more particularly relates to natural rubber, synthetic polyisoprene, polychloroprene, polybutadiene, polystyrene-butadiene and nitrile surgeon's gloves. A method for making the disclosed elastomeric articles is also provided.

BACKGROUND OF THE INVENTION

Elastomeric surgeon's gloves have very demanding requirements. They should have film strength to resist tearing, low thickness to allow touch sensitivity, and enough flexibility to handle a medical tool. Furthermore, they should be easy to don with both wet and dry hands, but not be slippery when handling instruments. Traditionally, surgeon's gloves have been manufactured by dipping hand-shaped molds into baths containing natural rubber latex, polyisoprene latex, nitrile latex, polychloroprene latex, and polystyrene butadiene latex to form a film of the desired thickness. The film is then cured and removed from the mold as a glove. Numerous problems are associated with the manufacturing of such elastomeric gloves. Removal of the gloves from the mold can be difficult because the gloves tend to be tacky and may adhere to the mold. In addition, the gloves adhere to themselves and prove difficult for a surgeon to don. Techniques for addressing these problems have been developed over the years. Initially, in order to strip a glove off a mold, powders were dusted onto the surface of the mold and the outer surface of the glove. Since the gloves are generally turned inside out as they are stripped from the molds, these powders then aid the subsequent donning of the glove by a surgeon. A wide variety of powders have been used including talc, lycopodium, calcium carbonate, starch and modified starch. Granuloma formation in patients was identified and attributed to powders, particularly when using talc and its use has long since been abandoned. As an alternate to powder, there are many disclosures of coating or treatments of gloves to modify their surface properties. These surface modifications have enjoyed some degrees of success. There are two general ways to accomplish the surface modifications: chemical treatment and coating materials onto a glove surface. Chlorination is representative of the chemical treatment. Chlorination renders a rubber surface slippery, but it is most effective in dry hand donning and additionally, the treatment may weaken and em brittle the overall film. It may also adversely affect the shelf life of a sterile glove. There are many disclosures relating to coating materials onto a rubber surface to improve its slip characteristics with both wet and dry skin. Representatives of the disclosures are as follows:

U.S. Pat. No. 4,575,476 to Podell, et al. describes a dipped rubber article having a skin contacting surface layer formed of a hydrogel polymer. Gloves prepared according to the teaching of Podell, et al. partially delaminate and release particles from the hydrogel coating. Furthermore, they tend to be somewhat thicker than many commercial gloves, thereby adversely affecting tactile sensitivity.

U.S. Pat. No. 5,612,083 to Haung, et al. demonstrates that a multi-layer flexible article includes a first layer of natural rubber; a second layer of natural rubber, polyurethane, poly(acrylamide-acrylic acid, sodium salt) and polyethylene oxide; and a third layer of acrylic copolymer and fluorocarbon telomer resin. These polymers as demonstrated by Haung, et al. do not have crosslinking characteristics to hydrate and hold at least 200% of water. The patient contacting surface of this technology is also very tacky when compared to the glove produced from the present invention.

U.S. Pat. No. 6,706,313 to Goldstein, et al. describes a water soluble hydrophilic resin and a method of application to natural rubber and synthetic latex products. Gloves prepared according to the teaching of Goldstein, et al. have low mechanical strength and loose particles from the coating. Furthermore, they tend to be somewhat thicker than many commercial gloves, thereby adversely affecting tactile sensitivity. U.S. Pat. No. 8,110,266 to Chen, et al. demonstrates that the internal surface of an elastomeric article is coated with a polyisoprene coating. This patent does not mention a third layer of hydrophilic polymer as the present invention to crosslink and form an uneven surface, thereby rendering the article substantially less textured and less comfortable in wear compared to articles as prepared and treated in the present invention.

U.S. Pat. No. 9,579,426 to Chen, et al. describes that the internal surface of the elastomeric article is coated with a polyisoprene coating. This patent does not mention a third layer of hydrophilic polymer as the present invention to effectively swell into enlarged water gel during washing, leach out allergenic impurities and shrink back to form an uneven surface after drying, thereby rendering the article substantially more toxic and less comfortable in wear compared to articles as prepared and treated by the present invention.

U.S. Patent Application No. 20170107403 to Woo, et al. shows a water-based hydrogel polymer coating and a method of application to natural rubber or other elastomeric latex products. This application does not mention hydrophilic polymers in the second and the third layers as the present invention which allow the glove to effectively swell into enlarged water gel during washing, leach out allergenic impurities, and shrink back to form an uneven surface after drying, thereby rendering the article substantially more toxic and less comfortable in wear compared to articles as prepared and treated in the present invention.

None of the foregoing examples disclose a multilayered process to make an elastomeric article with hydrophobic polymers as a patient contacting layer, hydrophilic polymers as a wearer contacting layer, and the polymers blended from both layers of polymers as an intermediate layer between two contacting layers. The hydrophilic polymers are cross-linked. Consequently, they texturize a wearer contacting surface, increase water absorption capability, and boost leaching effectiveness. The textured surface reduces contact points for the hand to slide in and out. Therefore, the friction force between hand and glove surface is significantly reduced. High water absorption minimizes the uncomfortable feeling from excessive sweating. The effectiveness in leaching makes the article less cytotoxic and more suitable for wearing.

SUMMARY

A multilayered elastomeric article comprises three different layers. A first layer as a patient contacting surface is formed with hydrophobic polymers selected from one, two, or more polymers from natural rubber, polyisoprene, nitrile, polystyrene/butadiene latex and polychloroprene. A third layer as a wearer contacting surface is formed with hydrophilic polymers selected from one, two, or more polymers from polyvinylpyrrolidone/vinylacetate copolymer, polyethylene glycol, polyethylene oxide, polyhydroxyethyl acrylate/acrylic acid copolymer, polyhydroxylethy acrylate/hydroxyethyl methacrylate/acrylic acid copolymer, polyacrylic acid, polyhydroxypropyl acrylate/acrylic acid copolymer, polyacrylic amide, polyhydroxyethyl acrylate/acrylic amide copolymer, polyacetoacetylethyl methacrylate, polylinoleyl acrylate, polybenzophenone methacrylate, polyacrylate copolymer, polyurethane, polyvinyl alcohol, polyvinyl acetate, polyisocyanate and polycarbodiimide. acrylic copolymer, silicone emulsion and fuorocarbon telomer resin. A second layer as an intermediate layer between the first and the third layers is formed with a blend of the polymers from both layers.

The article may be a multilayered surgeon's glove formed by dipping a hand shaped mold in a series of baths to form a first, a second, and a third layers. The layers on a glove mold are washed, dried and cured to form a unitary glove, then the surface of the first layer of the glove is turned outward as it is removed from the mold. The glove is further washed and chlorinated. The preferred gloves are donnable by wet and dry hands and have greater strength compared to existing gloves. The gloves are dipped three times in three different solutions. It is expected to substantially reduce the occurrence of air pinhole defects in manufacturing the gloves when compared to other commercial gloves.

DRAWINGS

FIG. 1 is a flow diagram of one embodiment of the process of the present invention.

FIG. 2A is a perspective view of a finished glove 2.

FIG. 2B is an enlarged sectional view of a finished glove taken along line A-A.

FIG. 3 is a graph comparing insoluble ratio at different cure temperatures.

FIG. 4 is a graph comparing water absorption at different cure temperatures.

FIG. 5 is a close-up SEM image taken at the surface of the third layer of a glove 2.

DETAILED DESCRIPTION

In accordance with the present invention, a preferred embodiment is a surgeon's glove formed on the surface of a mold. The glove molds are typically cast for the right and the left hand shapes and made in a variety of hand sizes from small to large. The molds are preferably made of ceramic, most preferably porcelain with a bisque or glazed surface finishing, but other materials such as stainless steel, glass, hardwoods, and plastic may also be used.

FIG. 1 illustrates a process flow diagram of one embodiment of the present invention.

FIG. 2A shows a perspective view of a finished glove 2 with line A-A for a sectional view in FIG. 2B.

The porcelain molds are cleaned in Step 1 in a bath with aqueous sodium hypochlorite about 2 to 6% and then rinsed with water about 120 to 150° F. The rinsed molds are then dipped in Step 2 in a coagulant about 110-160° F. Suitable coagulants include, but are not limited to, calcium nitrate, calcium chloride, acetic acid, magnesium acetate, and the like. A bath in step 2 is an aqueous solution with calcium nitrate about 20 to 25% and with octoxynol-9 about 0.1 to 2.0%. The molds with the coagulant on their surface are dried in step 3 about 150 to 200° F. for 5 to 10 minutes and then dipped into a bath containing an aqueous anionic hydrophobic polymer dispersion in Step 4. When the mold is dipped in the latex bath, the coagulant on the mold causes the latex to become unstable and gelled. A patient contacting layer of first layer 21 serving as a substrate for subsequently dipped layers is formed on the surface of the coagulant coated mold. The thickness of the first layer 21 and the subsequently dipped layers is generally governed by the solids content of the latex, the quantity of the coagulant deposited on the mold, the temperature of the mold and the residence time of the mold in the baths in a preferred embodiment. The bath in Step 4 has a total solids content of to 35%, a temperature of 70 to 80° F., and a pH of 8 to 11. The mold remains in the bath about 10 to 30 seconds, is then removed, and stays in air about 30-60 seconds for the latex film to gel. This dipping in Step 4 forms the first layer 21. The mold with the first layer on its surface is now dipped into a bath in Step 5 containing an aqueous polymer dispersion of the hydrophobic polymers from the first layer and the hydrophilic polymers from the third layer. The bath has a solids content of 8 to 20%, a temperature of 70° to 80° F., and a pH of 7 to 10. The proportions in parts per hundred of the components of the bath are anionic hydrophobic polymers from the first layer of 4 to 10, hydrophilic polymers from the third layer of 4 to 10, and water of 80 to 92. The mold remaining in the bath approximately 1 to 20 seconds is then removed from the bath in step 5 and dried in Step 6 about 100° to 180° F. for 160 to 260 seconds. This dipping in Step 5 forms an intermediate or a second layer 22. Following the formation of the second layer 22 over the first layer 21 on the surface of the mold, the mold with both layers (21 & 22) on its surface is dried in Step 6, washed and leached in Step 7 in water about 120 to 150° F. for 5 to 20 minutes. After drying, the washed and dried mold with the layers on its surface has a wearer contacting layer or third layer 23 applied over the second layer 22 by dipping the mold into a bath in Step 8 containing an aqueous hydrophilic polymer dispersion. The bath has a total solids content preferably between 1 to 10% and a composition in parts per hundred of hydrophilic polymers of 1 to 10 and water, preferably of 90 to 99. The bath has a pH about 3 to 10. After dipping the mold remains in the bath for 10 to 45 seconds and then is withdrawn. The mold with the three layers on its surface is then dried and cured in Step 9 at 210 to 240° F. for 30 to 50 minutes. This drying and curing step integrates the three layers into a unitary structure and completes the formation of the glove. The gloves are then stripped off the molds in Step 10 by inverting them, having the effect of placing the last formed third layer 23 inward. Preferably, the gloves are further tumbled with a lubricant, most preferably 170 polydimethylsiloxane, in Step 11. Following the treatment in Step 11, the gloves are preferably inverted in Step 12 and turned the third layer 23 outward. The gloves are subjected to a chlorination cycle in Step 13 for 15 to 60 minutes with a chlorination concentration about 100 to 300 ppm, and then tumbled with a lubricant in Step 14. Preferably, the gloves are tumbled with lanolin alkoxyether, lanolin oil alkoxy ether, fluorocarbon telomer, silicone, and the like, most preferably polydimethylsiloxane and Aloe Vera, and dried in Step 15 at 140 to 160° F. for 12 to 18 minutes. The gloves are inverted again in Step 16 with the third layer 23 inward and ready for inspection and packaging.

FIG. 2B presents a sectional view of the present invention along line A-A of FIG. 2A. The first layer 21 formed on the glove mold becomes the outside layer of a finished glove 2. The third layer 23 last formed on the glove mold is the inside layer of a finished glove.

One of the selection criteria for hydrophobic polymers of the first layer in Step 4 is natural rubber latex well known to have protein components, which are believed to be responsible for some allergic reactions to articles formed from natural rubber latex. However, synthetic polyisoprene, nitrile, polychloroprene and polystyrene-butadiene latexes do not contain any protein component, rather they contain a lot of process aids for forming elastomeric articles. These chemicals can induce chemical irritations. The washing and chlorination in Step 13 significantly reduces the impure components as well as any other water extractable allergenic or irritating moieties present when compared to gloves not so produced with the second layer 22 and the third layer 23. The hydrophilic polymers in the second and the third layers help water to penetrate through and also improve the efficacy of removal of impurities and allergenic moieties imbedded in the first layer.

The ability of a material to cause irritation has historically been measured by the degree of irritation to cell culture and correlated well with the results obtained from cell culture. An in vitro biocompatibility study, based on ANSI/AAMI/ISO 10993-5: 2009, was conducted on the test articles to determine the potential for cytotoxicity. A single extract of the test article was prepared using single strength Minimum Essential Medium supplemented with 5% serum and 2% antibiotics (1×MEM). This test extract was placed onto three separate monolayers of L-929 mouse fibroblast cells propagated in 5% $CO_2$. Three separate monolayers were prepared for the reagent control, negative control, and for the positive control. All monolayers were incubated at 37° C. in the presence of 5% $CO_2$ for 24 hours. The monolayers in the test, reagent control, negative control, and positive control wells were examined microscopically at 24 hours to determine any change in cell morphology. The reagent control, negative control and the positive control performed as anticipated. The glove described in the present invention can be washed and leached to become non-toxic when compared to commercial gloves.

Gloves manufactured according to the above described method are substantially more wet-hand and dry-hand donnable when compared to commercial gloves of equivalent thickness and design. The intermediate layer and the wearer contacting layer applied to the hydrophobic substrate can be used to impart a wet-slip and a dry-slip property to articles. When the three layers are coupled with the water washing and chlorination process steps, the detectable allergenic moieties from the hydrophobic polymers may be substantially reduced. Furthermore, the concentration of any other water extractable moieties having allergenic or chemical irritant potential present in the article may be substantially reduced.

A glove 2 manufactured according to the present invention should preferably have a patient contacting layer 21 approximately 0.10 to 0.40 mm thick, an intermediate layer 22 approximately 0.01 to 0.20 mm thick, and a wearer contacting layer 23 about 0.001 to 0.1 mm thick. Another benefit of the present invention is a reduced incidence of the "air pinhole" defect experienced in glove manufacturing. In a well-run glove manufacturing operation, it is generally recognized that there is some running level of various defects. A defect level of about three per one thousand gloves has historically been seen for the "air pinhole" defect for the manufacturing of gloves. In the case of the present invention, a substantial reduction of the "air pinhole" defect is achieved by repeatedly dipping three times in aqueous solutions. In producing the present invention a reduction in the occurrence of the "air pinhole" defect to below one in one thousand gloves may be achieved, thereby greatly increasing the yield for the process. The application of the second 22 and the third 23 layers over the first layer 21 in the multilayered glove may occlude many of the "air pinholes" present in the first layer, thereby reducing the occurrence of the "air pinhole" defect.

A preferred method for the manufacturing of the present invention is shown in FIG. 1 as an example. It should be recognized that the components and the parameters presented here are to be considered exemplary of the principles of the invention and are not intended to limit the invention to those components and parameters illustrated. The scope of the invention will be measured by the appended claims and their equivalents.

Hydrophobic polymers of the first layer were cured at 100-120° C. for 60 minutes, and they were soaked in water for 30 minutes. Excess water was removed, the polymer saturated with water was weighed (W1), and then water was dried out at an oven to weigh the polymer (W2). Water absorption is reported as (W1−W2)/W2.

TABLE 1

| Water Absorption | | |
|---|---|---|
| | Natural rubber latex | Synthetic latex |
| % | 0.2-0.6 | 0.4-0.9 |

The hydrophobic polymers used in the first layer 21 of the present invention swell and retain less than 1% of water as demonstrated in TABLE 1. A first layer is designed to be less hydrated. Hydrated first layer has lower mechanical strength as well as lower chemical and electric resistance. A first layer with lower electrical resistance has a higher potential to introduce electrical shock and burn during a surgical procedure. A first layer with a feature of lower water retention could also prevent viruses and other harmful small molecules from passing through.

Hydrophobic polymers can be categorized as natural rubber latexes and synthetic latexes. Natural rubber latex is tapped from the Hevea Brasiliensis rubber tree and stabilized by protein. Contact dermatitis, type IV hypersensitivity, and type I immediate hypersensitivity of allergenic reactions can occur in users using natural rubber latex products and have resulted in an increased demand for synthetic latexes. Synthetic latexes include styrene butadiene, acrylonitrile butadiene, polychloroprene, butyl, and polyisoprene. The sulfur vulcanization system as shown in TABLE 2 is typically used to cure the hydrophobic polymers into a crosslinked elastomer. Accelerators are classified in thiazole, dithiocarbamate, and amine types. Mixtures of accelerators are often used to control the rate of vulcanization and achieve desired physical properties of finished articles.

TABLE 2

| A formulation for Hydrophobic polymers | |
|---|---|
| Materials | Parts |
| Hydrophobic polymers | 100 |
| Sulfur | 0.5-2 |
| Zinc oxide | 0.2-5 |
| Accelerator | 0.1-4 |

Typical physical properties obtained from the test method of ASTM D412-16 are listed in TABLE 3. The results meet ASTM D-3577-09 standard for the requirements of disposal surgical gloves.

TABLE 3

Physical Properties for Hydrophobic polymers

| Physical Properties | Natural rubber latex | Synthetic latex |
|---|---|---|
| Tensile, psi | 4100-4900 | 2600-3200 |
| Elongation, % | 810-910 | 700-1000 |
| 500% Modulus, psi | 400-500 | 250-500 |
| Tear, pli | 250-300 | 150-300 |

After the first layer of hydrophobic polymers is formed, hydrophilic polymers included in the second 22 and the third 23 layers are crosslinked in Step 9 of drying and curing. Crosslinked hydrophilic polymer materials can hold large amounts of water and are resistant to dissolving.

Hydrophilic polymers can be derived from nature products or polymer synthesis. Hydrophilic polymers are synthesized by a single monomer or by two or more different monomers or by interpenetrating two complete different polymer networks. Acrylic polymers are used for forming hydrophilic polymers in the second and the third layers. Acrylic polymers as described in the present invention are cross-linkable. Crosslinking is achieved through the inclusion of hydroxyl, carboxyl, and/or self-crosslinking functionalities in the polymer backbone. Self-crosslinking is crosslinked through unsaturation double bonds or chemical condensation and addition reactions. Hydroxyl functionality is cross-linked with amino resins and isocyanates. Carboxyl functionality is cross-linked through carbodiimides, aziridines, and epoxides. Hydrophilic polymers are a blend of a hydroxyl-functional polymer with an amino acrylate polymer.

The second layer 22 in Step 5 is formed from a mixture of the hydrophobic and the hydrophilic polymers and diluted to a solids content of 10-20%. High ratio of hydrophilic to hydrophobic polymers creates more uneven surface. The optimized ratio is about 30-70%. Finished gloves can be stretched to 700% and show no cracking on the surface during stretching. Typical physical properties of the second layer are: tensile, 2000-3500 psi and elongation, 500-900%

The third layer 23 in Step 8 is formed from a mixture of one or two or three hydrophilic polymers and diluted to a solids content of 1-10%. The dispersion can be crosslinked in acidic or alkali conditions. Dispersions of pH 4.1 and pH 9.1 are studied. Ammonia is used to raise a pH value. The dispersion before crosslinking is soluble in water and becomes insoluble after crosslinking. Insoluble experiments are conducted to indicate how much the degree of crosslinking may proceed. The experimental method is described as follows:

1. Weigh approximately 5-6 grams (W1) of the polymer solution, dry overnight at room temperature, and then cure at different temperatures and times.
2. Determine a solids content of the polymer solution (S1).
3. Soak and disperse the cured films in 20-25 grams of water for 30 minutes, then filter through a preweighed filter paper (W2), dry and weigh the paper with insoluble polymer (W3).
4. Determine an insoluble ratio by the equation of (W3−W2) (W1*S1).

FIG. 3 illustrates the results of insoluble ratio of pH 4.1 and 9.1 dispersions at different cure temperatures for 15 minutes. An increase in cure temperature increases the values of insoluble ratio. The pH 4.1 dispersion has a higher insoluble ratio than the pH 9.1 dispersion. The pH 4.1 dispersion achieves an insoluble ratio of 0.97 at 100° C. for 15 minutes. The pH 9.1 dispersion increases its insoluble ratio from 0 to 0.62 in 15 minutes of curing at 80° C. The results of insoluble ratio demonstrate that both dispersions can be crosslinked.

Hydrophilic polymers in dispersions were cured at different temperatures for 60 minutes, they were soaked in water for 30 minutes. Excess water was removed, the polymer saturated with water was weighed (W1), and then water was dried out at an oven to weigh the polymer (W2). Water absorption is reported as (W1−W2)/W2, FIG. 4 shows that the pH 9.1 dispersion has much higher water absorption than the pH 4.1 dispersion. Also, an increase in cure temperature significantly decreases water absorption for the pH 9.1 dispersion but not for the pH 4.1 solution. The hydrophilic polymers contain carboxylic acid functional groups. In an acidic condition, the hydrophilic polymers likely display tightly coiled molecules. Once neutralized, the molecules begin to uncoil and stretch from negative charge repulsion. The neutralized acid groups are ionic in nature, strongly absorb water, and achieve maximum water absorption. High temperatures drive ammonia away and form less uncoiled and ionic molecules. Therefore, water absorption per gram of crosslinked hydrophilic polymer of the pH 9.1 dispersion decreases from 27.7 g (2770%) at 80° C., 16.8 g (1680%) at 100° C., 13 g (1300%) at 120° C. to 3.4 g (340%) at 140° C. The pH 4.1 dispersion has almost constant water absorption of 2.4-2.5 g (240-250%) through all cure temperatures. The hydrophilic polymers as demonstrated by the present invention can swell and retain at least 240% of water at acidic conditions and 340% at alkali conditions. During washing and chlorination, the swollen gel formed from the hydrophilic polymers on the second and third layers helps to remove allergenic moieties and irritant compounding chemicals from the multilayered article.

A finished glove 2 was extracted by using an acidic sweat buffer solution for 6 hours. Extracted chemicals were determined quantitatively using HPLC. The estimated detectable limits were 2 ug/g for accelerators. After washing and chlorination, a finished glove 2 as produced in the present invention has accelerator residues below the detected limits when compared to other commercial gloves.

FIG. 5 provides a close-up SEM image taken at the surface of the third layer of a finished glove 2. Water is evaporated out during curing and drying cycles. The shrinkage of dynamic volume from a swollen state to dry creates a textured surface as shown in FIG. 5. The textured surface provides the hand with sufficient room to breathe and minimizes the uncomfortable feeling from excessive swelling.

What is claimed:
1. A multilayered elastomeric article, comprising:
a first layer comprising a patient contacting surface, the first layer formed from an aqueous dispersion of hydrophobic polymers, wherein the aqueous dispersion of hydrophobic polymers forming the first layer has a total solids content of 20-35% and a pH of 7-12, the first layer comprising at least one crosslinked polymer selected from the group consisting of natural rubber, synthetic polyisoprene, nitrile, polybutadiene, polystyrene-butadiene, and polychloroprene;
a third layer comprising a wearer contacting surface, the third layer formed from an aqueous dispersion of hydrophilic polymers, the third layer having a total solids content of 1-10% and a pH of 3-10, the third layer comprising at least one crosslinked polymer selected from the group consisting of polyvinylpyrrolidone/vinylacetate copolymer, polyethylene glycol, polyethylene oxide, polyhydroxyethyl acrylate, polyacrylic acid, polyhydroxyethyl acrylate/acrylic acid copolymer, polyhydroxyethyl acrylate/methacrylic acid copolymer, polyhydroxyethyl acrylate/hydroxyethyl methacrylate/acrylic acid copolymer, polyhydroxypropyl acrylate/hydroxyethyl methacrylate/acrylic acid copolymer, polyacrylic amide, polyhydroxyethyl acrylate/acrylic amide copolymer, polyacetoacetylethyl methacrylate, polyacetoacetyl ethyl methacrylate/hydroxyl ethyl acrylate/acrylate acid, polylinoleyl acrylate, polylinoleyl acrylate/hydroxyl ethyl acrylate, polybenzophenone methacrylate, polyacrylate copolymer, polyurethane, polyvinyl alcohol, polyvinyl acetate, melamine, polyisocyanate and polycarbodiimide;

a second layer that is an intermediate layer between the first and the third layers, the second layer being formed from an aqueous dispersion of crosslinked polymers from the first and the third layers, wherein the second layer consists of crosslinked polymers selected from at least one polymer from the first layer and at least one polymer from the third layer, and wherein the aqueous dispersion forming the second layer has a total solids content of 10-20% and a pH of 6-11, and comprises 30-70% hydrophobic polymers of the first layer, and 30-70% hydrophilic polymers of the third layer.

2. The multilayered elastomeric article of claim 1 wherein the hydrophobic polymers of the first layer are crosslinked through at least one selected from the group consisting of carboxyl groups, hydroxyl groups, sulfur, peroxide, ionic or e-beam, ultra violet, oxidation, and radiation, thereby rendering the first layer hydrophobic and subsequently allowing it to absorb less than 1% water.

3. The multilayered elastomeric article of claim 1 wherein the hydrophilic polymers of the third layer are crosslinked through at least one selected from the group consisting of carboxyl groups, hydroxyl groups, sulfur, peroxide, ionic or e-beam, ultra violet, oxidation, and radiation, thereby rendering the third layer hydrophilic and subsequently able to absorb more than 200% water compared to its mass.

4. The multilayered elastomeric article of claim 1 further includes a lubricant coating consisting of at least one selected from the group consisting of silicone, fluorocarbon telomer, lanolin oil, alkoxy ethers, Aloe Vera, and lanolin alkoxy ethers to the surfaces of the first layer and third layer.

* * * * *